US009192286B2

(12) United States Patent
Kazakevich et al.

(10) Patent No.: US 9,192,286 B2
(45) Date of Patent: Nov. 24, 2015

(54) STEREOSCOPIC VISUALIZATION SYSTEM (75) Inventors: Yuri Kazakevich, Newton, MA (US); John E. Kennedy, Lowell, MA (US)

(73) Assignee: Viking Systems, Inc., Westborough, MA (US)

( * ) Notice: Subject to any disclaimer, the term of this patent is extended or adjusted under 35 U.S.C. 154(b) by 1123 days.

(21) Appl. No.: 13/047,708

(22) Filed: Mar. 14, 2011

(65) Prior Publication Data

US 2011/0228049 A1  Sep. 22, 2011

Related U.S. Application Data

(60) Provisional application No. 61/313,220, filed on Mar. 12, 2010.

(51) Int. Cl.
*H04N 13/00* (2006.01)
*A61B 1/00* (2006.01)
*A61B 1/04* (2006.01)

(52) U.S. Cl.
CPC ........... *A61B 1/00193* (2013.01); *A61B 1/0005* (2013.01); *A61B 1/00188* (2013.01); *A61B 1/042* (2013.01)

(58) Field of Classification Search
CPC .................. A61B 1/00193; G02B 23/2415
USPC .......................................................... 348/45
IPC ................................... A61B 1/00; H04N 13/00
See application file for complete search history.

(56) References Cited

U.S. PATENT DOCUMENTS

| | | | |
|---|---|---|---|
| 2,906,183 A | 9/1959 | Rochwite | |
| 3,520,587 A | 7/1970 | Tasaki et al. | |
| 5,122,650 A | 6/1992 | McKinley | |
| 5,191,203 A | 3/1993 | McKinley | |
| 5,577,991 A * | 11/1996 | Akui et al. | 600/111 |
| 5,673,147 A | 9/1997 | McKinley | |
| 5,776,049 A * | 7/1998 | Takahashi | 600/111 |
| 5,860,912 A | 1/1999 | Chiba | |
| 6,219,182 B1 | 4/2001 | McKinley | |
| 7,405,877 B1 * | 7/2008 | Schechterman | 359/465 |
| 2005/0089212 A1 * | 4/2005 | Mashitani et al. | 382/154 |
| 2008/0049100 A1 | 2/2008 | Lipton et al. | |
| 2009/0096865 A1 | 4/2009 | McKinley | |

FOREIGN PATENT DOCUMENTS

GB 2160381 12/1985

OTHER PUBLICATIONS

Park, Soon-Yong et al., Stereoscopic imaging camera with simultaneous vergence and focus control, Optical Engineering, Dec. 2004, pp. 3130-3137, vol. 43, No. 12.

* cited by examiner

*Primary Examiner* — Jay Patel
*Assistant Examiner* — Yulin Sun
(74) *Attorney, Agent, or Firm* — Pandiscio & Pandiscio (57) ABSTRACT

Apparatus for presenting a stereoscopic image to a viewer, the apparatus including an endoscope; and a stereoscopic video camera optically connected to the endoscope, wherein the stereoscopic video camera includes first and second optical channels for acquiring, respectively, first and second images of a scene from the endoscope; first and second image sensors for acquiring, respectively, the first and second images from the first and second optical channels, the first and second image sensors being positioned along an axis; and parallax adjusting means for adjusting the parallax of a stereoscopic image acquired by the first and second image sensors and presented on a display.

31 Claims, 9 Drawing Sheets

First-order optical lay-out of dual-channel stereo camera

Kinematical Diagram of Exemplary Embodiment

FIG. 8

Dual Channel Endoscope and Camera Head Modules

FIG. 9

Single Channel Endoscope and Camera Head Modules

STEREOSCOPIC VISUALIZATION SYSTEM

REFERENCE TO PENDING PRIOR PATENT APPLICATION

This patent application claims benefit of prior U.S. Provisional Patent Application Ser. No. 61/313,220, filed Mar. 12, 2010 by Yuri Kazakevich et al. for STEREOSCOPIC VIDEO CAMERA, which patent application is hereby incorporated herein by reference.

FIELD OF THE INVENTION

This invention relates to visualization systems in general, and more particularly to stereoscopic visualization systems.

BACKGROUND OF THE INVENTION

One of the main problems associated with stereoscopic television is the disruption of the normal correlation between human eye accommodation and vergence between the two eyes of the viewer. Specifically, in normal visual experience, the human eyes are accommodated (i.e., focused) to the object of observation and, at the same time, the two eyes are converged on the same object. Therefore the object of observation is projected on corresponding areas of the two retinas with no disparity. All of the objects in front of the object of observation will have crossed disparity and will be sensed as "closer", whereas all of the objects behind the object of observation will have uncrossed disparity and will be sensed as "farther away".

Figure 1:
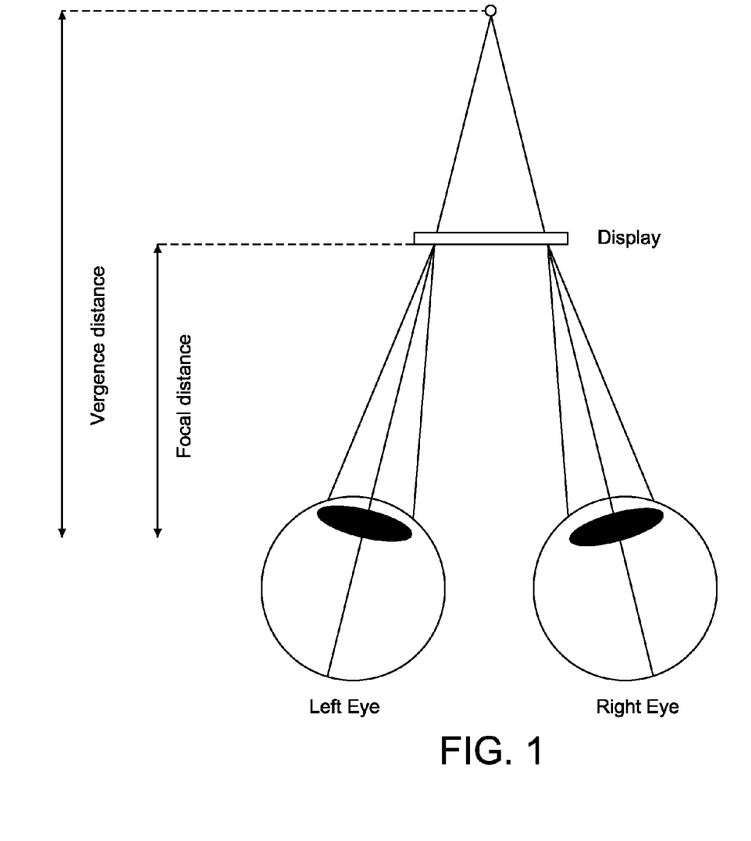
FIG. 1 is a schematic view illustrating a typical stereoscopic scenario in which there is a deviation in the normal correspondence between focal distance and vergence distance.
Figure 2:
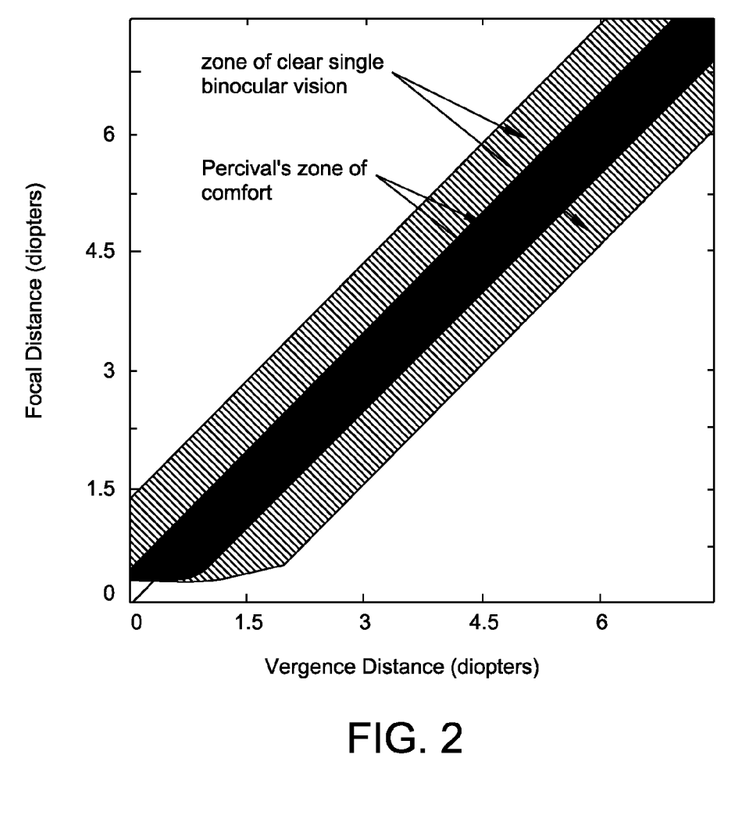
FIG. 2 is a schematic view which illustrates how the relationship between the focal distance and the vergence distance should remain within certain bounds in order for the viewer to remain in their "zone of comfort" (i.e., the so-called "Percival's zone of comfort")

However, this correlation between the focusing of the eyes and their convergence is usually disrupted in stereoscopic video applications. In this case, the left and right representations of objects are physically located on the surface of the monitor as opposed to arbitrary places in space for regular visual experiences. So, in order to obtain the best focus, the eyes need to optically focus at the monitor. However, the vergence of the two eyes is dictated by the parallax generated between the left and right images on the monitor and generally does not correspond to the eye accommodation for the best focus in the monitor plane. See FIG. 1, which illustrates a typical stereoscopic scenario in which there is a deviation in the normal correspondence between focal distance and vergence distance. This break in the linkage between eye focus and convergence causes eye strain and fatigue for the viewer. See also FIG. 2, which illustrates how the relationship between focal distance and the vergence distance should remain within certain bounds in order for the viewer to remain in their "zone of comfort" (i.e., the so-called "Percival's zone of comfort").

The problem described above becomes particularly important in medical (e.g., endoscopic) applications where the stereoscopic video system may be used for precision viewing for prolonged periods of time. By way of example but not limitation, it is not uncommon for surgical cases to last over 2 hours, and typically a surgeon performs at least several cases a day. Due to the critical nature of such medical applications, it is important to minimize user fatigue and provide for comfortable visualization while retaining all of the benefits of depth perception.

Figure 3:
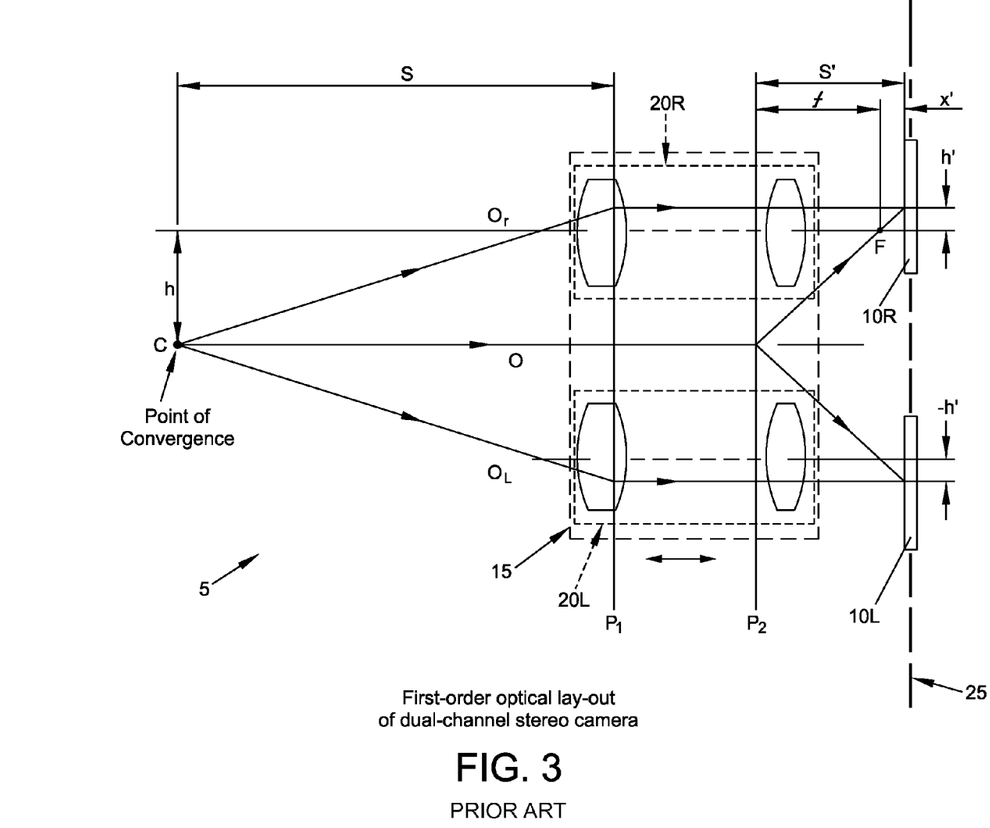
FIG. 3 is a schematic view of a first-order optical layout of a typical dual-channel stereo camera.
Figure 4:
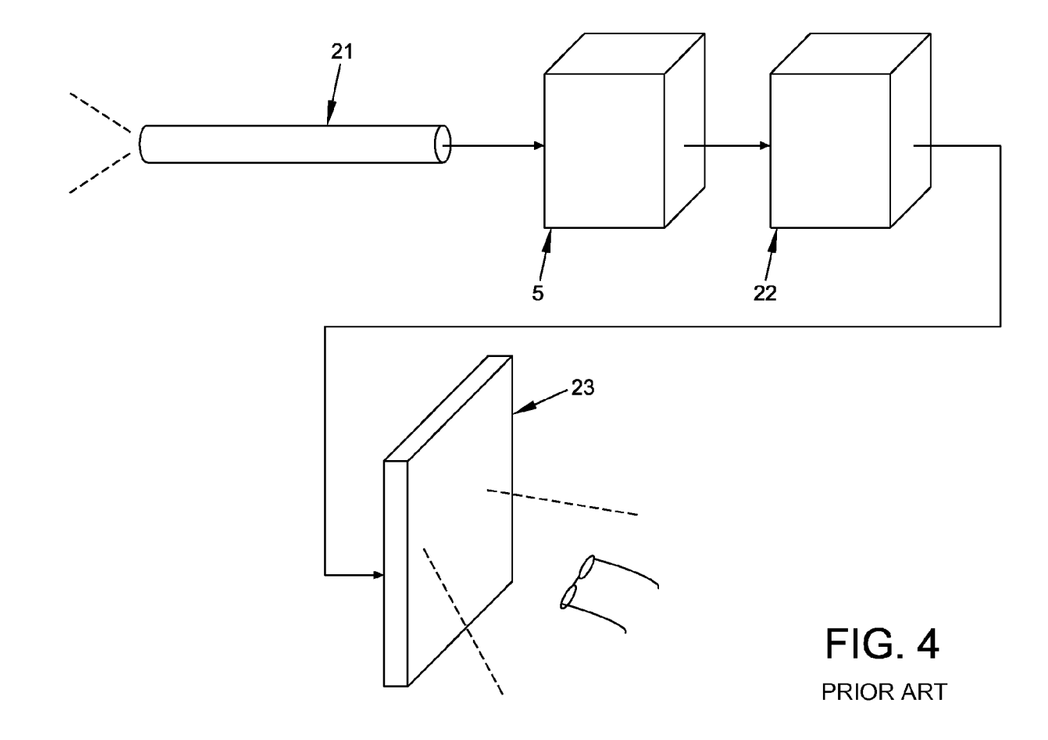
FIG. 4 is a schematic view of a typical stereoscopic visualization system.

FIG. 3 shows a first-order optical layout of a typical dual-channel stereo camera 5. Dual-channel stereo camera 5 generally comprises a left image sensor 10L and a right image sensor 10R (e.g., CCD or CMOS sensors), and an optical system 15 comprising a left channel optical system 20L and a right channel optical system 20R (shown schematically in FIG. 3 as two single lenses for each optical channel for clarity of illustration purposes only). As is well known in the art, and looking now at FIG. 4, dual-channel stereo camera 5 is intended to be coupled to an endoscope 21, the signals generated by image sensors 10L, 10R are forwarded to an appropriate electronic system 22 for processing (the electronic system 22 may be included within stereo camera 5), and then the processed signals are forwarded to an appropriate stereo display 23 or recording device configured to display or record the left and right images captured by the left and right image sensors 10L, 10R. This display device 23 may be a 3D monitor of the sort well known in the art, or a head-mounted display, or any other display device capable of presenting the left and right images to the appropriate eye of the viewer.

In FIG. 3:

$P_1$ and $P_2$ are the first and second principal planes of the left and right channel optical systems 20L, 20R—in the first-order approximation, the left and right channel optical systems 20L, 20R are considered identical and their corresponding principal planes coincident;

O is the median axis of the dual-channel stereo camera 5;

$O_L$ and $O_R$ are the optical axes of the left and right channel optical systems 20L, 20R, respectively;

f is the effective focal length of the dual-channel stereo camera 5;

s and s' are the distances from an object and its image to the corresponding principal planes—by the sign convention generally accepted in the optical field, distances measured to the left from a principal plane are considered negative and distances measured to the right from a principal plane are considered positive—thus, in FIG. 3, distance s is considered to be negative whereas distance s' is considered to be positive;

F is the back focal point of the dual-channel stereo camera 5;

x' is the distance from the focal point F to the image plane;

C is the point of convergence (see below);

h is the distance between the median axis O and the optical axis of the right channel optical system 20R—by the sign convention, the heights measured below the optical axis are considered negative while the heights measured above the optical axis are considered positive; and h' is the image height for the point of convergence.

Typically, a dual channel stereo camera is aligned for a certain point of convergence in the object space. The alignment is achieved by offsetting image sensors 10L, 10R in the "horizontal plane" of the eyes, i.e., the "horizontal plane" represented by the line 25 in FIG. 3. It can be seen from FIG. 3 that the centers of sensors 10L, 10R are offset horizontally from the optical axes $O_L$, $O_R$ of the left and right optical systems 20L, 20R so that the point of convergence is imaged at the centers of each corresponding sensor. Owing to such an arrangement, the point of convergence is displayed with zero parallax on the display device, so for this particular point, the link between the eye accommodation and the eye convergence will be preserved, and for this particular point of convergence, the dual-channel stereo camera will provide the viewer with a "normal" visual experience.

Typically the point of convergence is selected so as to be within the usable range of the object distances which are expected to be encountered in a particular application. For instance, point C may be chosen to be at a distance of 5 m from the optical system for a typical camcorder application, or at a distance of 50 mm from the distal tip of an endoscope for a general surgery laparoscopic application. Similarly, the distance between the optical axes $O_L$, $O_R$ of the left and right channel optical systems 20L, 20R, the focal lengths of the left and right optical systems 20L, 20R, and the types/sizes of image sensors 10L, 10R are typically selected in accordance with the application for which the stereo camera is to be used.

The drawback of a conventional stereo camera is that when the camera is focused to any other point which is at a distance different from the point of convergence, then the point in the center of the display device will have non-zero parallax, thereby breaking the normal link between eye accommodation and convergence. This break in the normal link between eye accommodation and convergence causes eye strain and fatigue for the viewer.

In some situations, e.g., where the conventional stereo camera only needs to be used for brief periods of time, and/or where it is not necessary to view an image with significant precision, and/or where the parallax is relatively nominal, this break in the normal link between eye accommodation and convergence may cause only modest levels of eye strain and fatigue for the viewer and a conventional stereo camera may be acceptable. However, in medical (e.g., endoscopic) applications where the stereo camera must be used for long periods of time, with great precision and where the parallax is frequently substantial, the break in the link between eye accommodation and convergence may cause significant levels of eye strain and fatigue for the viewer, and a conventional stereo camera may be unsatisfactory.

Thus there is a need for a new and improved stereoscopic visualization system which can address the foregoing issues of convergence in medical (e.g., endoscopic) and related applications.

SUMMARY OF THE INVENTION

The present invention provides a new and improved stereoscopic visualization system which can address the foregoing issues of convergence in medical (e.g., endoscopic) and related applications. Among other things, the present invention addresses the foregoing issues of convergence by providing the stereoscopic visualization system with means for adjusting the parallax of a stereoscopic image presented on a display.

In one form of the present invention, there is provided apparatus for presenting a stereoscopic image to a viewer, the apparatus comprising:
   an endoscope; and
   a stereoscopic video camera optically connected to the endoscope, wherein the stereoscopic video camera comprises:
      first and second optical channels for acquiring, respectively, first and second images of a scene from the endoscope;
      first and second image sensors for acquiring, respectively, the first and second images from the first and second optical channels, the first and second image sensors being positioned along an axis; and
      parallax adjusting means for adjusting the parallax of a stereoscopic image acquired by the first and second image sensors and presented on a display.

In another form of the present invention, there is provided apparatus for presenting a stereoscopic image to a viewer, the apparatus comprising:
   a stereoscopic video camera comprising:
      first and second optical channels for acquiring, respectively, first and second images of a scene;
      first and second image sensors for acquiring, respectively, the first and second images from the first and second optical channels, the first and second image sensors being positioned along an axis; and
      parallax adjusting means for adjusting the parallax of a stereoscopic image acquired by the first and second image sensors and presented on a display;
      wherein the first and second optical channels comprise first and second focal points, respectively, wherein the apparatus comprises focusing means for adjusting the dispositions of the first and second focal points, and further wherein the parallax adjusting means is configured to operate independently of the focusing means.

In another form of the present invention, there is provided apparatus for presenting a stereoscopic image to a viewer, the apparatus comprising:
   a stereoscopic video camera comprising:
      first and second optical channels for acquiring, respectively, first and second images of a scene;
      first and second image sensors for acquiring, respectively, the first and second images from the first and second optical channels, the first and second image sensors being positioned along an axis; and
      parallax adjusting means for adjusting the parallax of a stereoscopic image acquired by the first and second image sensors and presented on a display;
      wherein the first and second optical channels each comprises at least one optical component, and further wherein the parallax adjusting means comprises optical component movement means for physically moving at least one optical component of at least one of the first and second optical channels.

In another form of the present invention, there is provided apparatus for presenting a stereoscopic image to a viewer, the apparatus comprising:
   a stereoscopic video camera comprising:
      first and second optical channels for acquiring, respectively, first and second images of a scene;
      first and second image sensors for acquiring, respectively, the first and second images from the first and second optical channels, the first and second image sensors being positioned along an axis; and
      parallax adjusting means for adjusting the parallax of a stereoscopic image acquired by the first and second image sensors and presented on a display;
      wherein the apparatus further comprises mapping means for mapping the first and second images acquired by the first and second image sensors to a display according to a pre-determined positional relationship, and further wherein the parallax adjusting means is configured to modify the manner in which the mapping means maps the first and second images to the display.

In another form of the present invention, there is provided a method for presenting a stereoscopic image to a viewer, the method comprising:
   providing an endoscope, and a stereoscopic video camera optically connected to the endoscope, wherein the stereoscopic video camera comprises:
      first and second optical channels for acquiring, respectively, first and second images of a scene from the endoscope;
      first and second image sensors for acquiring, respectively, the first and second images from the first and second optical channels, the first and second image sensors being positioned along an axis; and
      parallax adjusting means for adjusting the parallax of a stereoscopic image acquired by the first and second image sensors and presented on a display; and operating the endoscope and the stereoscopic video camera so as to provide a stereoscopic image to the user wherein parallax has been adjusted.

In another form of the present invention, there is provided a method for presenting a stereoscopic image to a viewer, the method comprising:

providing a stereoscopic video camera comprising:
first and second optical channels for acquiring, respectively, first and second images of a scene;
first and second image sensors for acquiring, respectively, the first and second images from the first and second optical channels, the first and second image sensors being positioned along an axis; and
parallax adjusting means for adjusting the parallax of a stereoscopic image acquired by the first and second image sensors and presented on a display;
wherein the first and second optical channels comprise first and second focal points, respectively, wherein the apparatus comprises focusing means for adjusting the dispositions of the first and second focal points, and further wherein the parallax adjusting means is configured to operate independently of the focusing means; and
operating the endoscope and the stereoscopic video camera so as to provide a stereoscopic image to the user wherein parallax has been adjusted.

In another form of the present invention, there is provided a method for presenting a stereoscopic image to a viewer, the method comprising:

providing a stereoscopic video camera comprising:
first and second optical channels for acquiring, respectively, first and second images of a scene;
first and second image sensors for acquiring, respectively, the first and second images from the first and second optical channels, the first and second image sensors being positioned along an axis; and
parallax adjusting means for adjusting the parallax of a stereoscopic image acquired by the first and second image sensors and presented on a display;
wherein the first and second optical channels each comprises at least one optical component, and further wherein the parallax adjusting means comprises optical component movement means for physically moving at least one optical component of at least one of the first and second optical channels; and
operating the endoscope and the stereoscopic video camera so as to provide a stereoscopic image to the user wherein parallax has been adjusted.

In another form of the present invention, there is provided a method for presenting a stereoscopic image to a viewer, the method comprising:

providing a stereoscopic video camera comprising:
first and second optical channels for acquiring, respectively, the first and second images of a scene;
first and second image sensors for acquiring, respectively, the first and second images from the first and second optical channels, the first and second image sensors being positioned along an axis; and
parallax adjusting means for adjusting the parallax of a stereoscopic image acquired by the first and second image sensors and presented on a display;
wherein the apparatus further comprises mapping means for mapping the first and second images acquired by the first and second image sensors to a display according to a pre-determined positional relationship, and further wherein the parallax adjusting means is configured to modify the manner in which the mapping means maps the first and second images to the display; and
operating the endoscope and the stereoscopic video camera so as to provide a stereoscopic image to the user wherein parallax has been adjusted.

In another form of the present invention, there is provided apparatus for presenting a stereoscopic image to a viewer, the apparatus comprising:

a stereoscopic video system comprising:
first and second image sensors for acquiring, respectively, first and second images of a scene;
a display system for displaying the first image to the first eye of the viewer and the second image to the second eye of the viewer; and
parallax adjusting means for adjusting the parallax between the first and second images.

In another form of the present invention, there is provided a method for presenting a stereoscopic image to a viewer, the method comprising:

providing a stereoscopic video system comprising:
first and second image sensors for acquiring, respectively, first and second images of a scene;
a display system for displaying the first image to the first eye of the viewer and the second image to the second eye of the viewer; and
parallax adjusting means for adjusting the parallax between the first and second images; and
operating the stereoscopic video system so as to provide a stereoscopic image to the user wherein parallax has been adjusted.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Novel Stereoscopic Visualization System Wherein Parallax is Adjusted by Adjusting the Physical Dispositions of the Left Image Sensor and the Right Image Sensor in Accordance with the Focal Point of the Stereoscopic Visualization System Assuming that the user will most likely try to bring the image of the most important part of the scene (e.g., the tissue under treatment) into proper focus and into the center of the display, it is preferable to correlate focus and vergence for the center of the displayed image.

Figure 5:
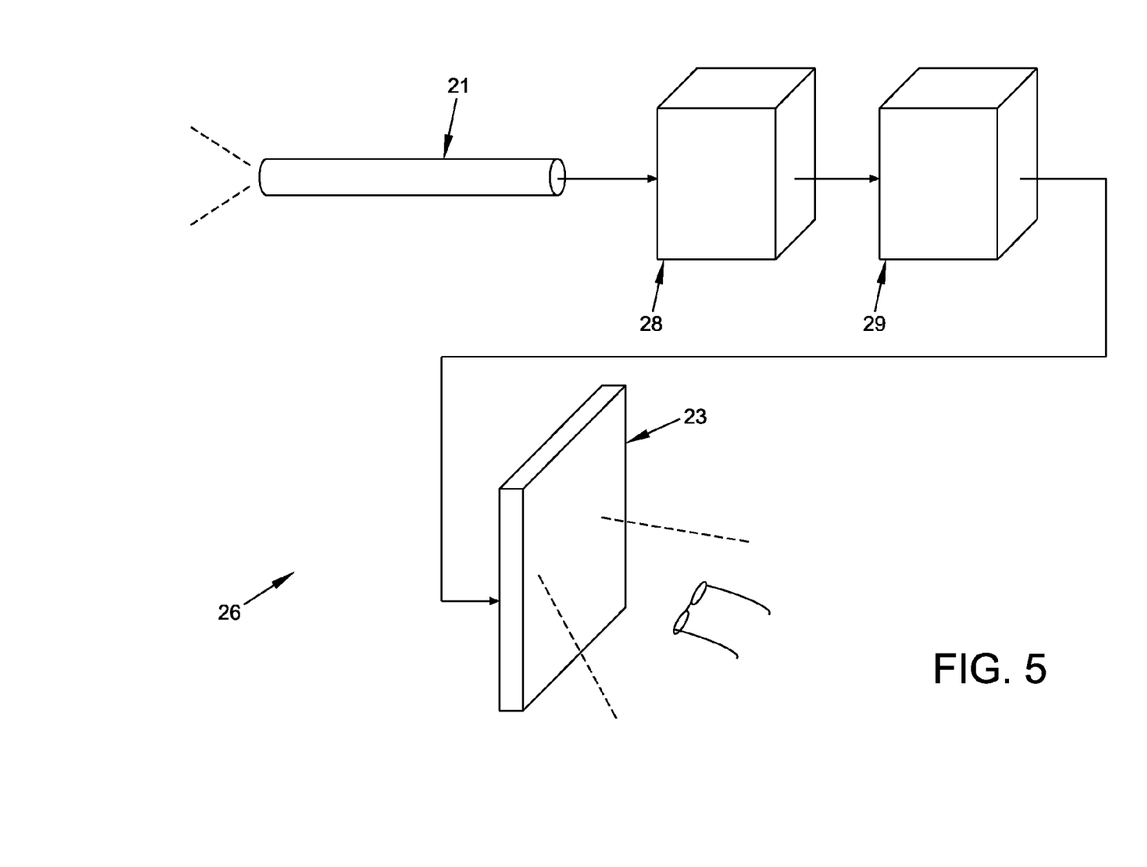
FIG. 5 is a schematic view of a novel stereoscopic visualization system formed in accordance with the present invention, wherein the novel stereoscopic visualization system comprises means for adjusting the parallax of a stereoscopic image presented on a display.

Thus, and looking now at FIG. 5, in one form of the present invention, there is provided a novel stereoscopic visualization system 26 which is configured to maintain the link between focus and vergence for the center of the displayed image. Stereoscopic visualization system 26 generally comprises the endoscope 21 for acquiring a stereo view of a scene, a novel stereo camera 28 for capturing the image obtained by endoscope 21, electronic processing apparatus 29 (which may be included within novel stereo camera 28), and an appropriate display 23.

First it can be seen from the geometry in FIG. 3 and from the principles of the first-order image formation:

$$h'=(h/f)x' \qquad (1)$$

When the object moves from a distance s from the first principle plane $P_1$ to some other distance, the optical system is refocused so that the image of the object is brought into focus again. To achieve this refocusing, the optical systems of both channels move as a unit along axis O. Suppose the object point C moves to a new position $C_1$ by a distance $\Delta s$. In order to refocus, the optical system will move by a distance $\Delta s'$. It is clear from FIG. 3 that as the object point C moves along the axis O, the value h does not change as it is defined by the inter-axis distance of the two channels (which is also called the stereo base of the stereoscopic optical system). It can also be seen that the focal point F will move together with the optical system by the same distance $\Delta s'$. The distance between the focal point and the image plane x' will therefore become $x'+\Delta s'$. Let the image height for the new object point $C_1$ be $h_1'$, then:

$$h_1'=(h/f)(x'+\Delta s') \qquad (2)$$

From equations (1) and (2) above, it follows that the difference between the original image height and the new image height is expressed by a simple linear function:

$$\Delta h'=(h/f)\Delta s' \qquad (3)$$

Thus, as the object point moves to a new position $C_1$, its image on each sensor moves horizontally in opposite directions by the distance $\Delta h'$ given by equation (3), therefore resulting in horizontal parallax of 2 $\Delta h'$ as measured in the sensor plane. The actual parallax in the display will be scaled according to magnification between the display device and the sensor.

As discussed above, this parallax will create eye strain and fatigue for the user. Inasmuch as the magnitude of this parallax may be substantial in endoscopic applications, and inasmuch as this parallax may be experienced by the surgeon for substantial periods of time in endoscopic applications, the eye strain and fatigue associated with this parallax may be significant, to the point of interfering with proper visualization of the surgical site.

The present invention provides means for eliminating (or adjusting) the parallax resulting from refocusing.

In one form of the invention, parallax can be eliminated (or adjusted) by effecting an appropriate "horizontal" displacement of the image sensors (i.e., along the line 25 of FIG. 3) so as to create an additional offset of $\Delta h'$ given by equation (3) for each sensor. Thus, in one form of the invention, novel stereo camera 28 is configured so that its two image sensors 10L, 10R will move in unison opposite to each other in the "horizontal" direction (i.e., along the line 25 of FIG. 3), and simultaneously with the optical system as the optical system focuses, in such a way that the axial "in-focus" object point will automatically become a convergence point, thereby providing visualization with zero parallax.

Figure 6:
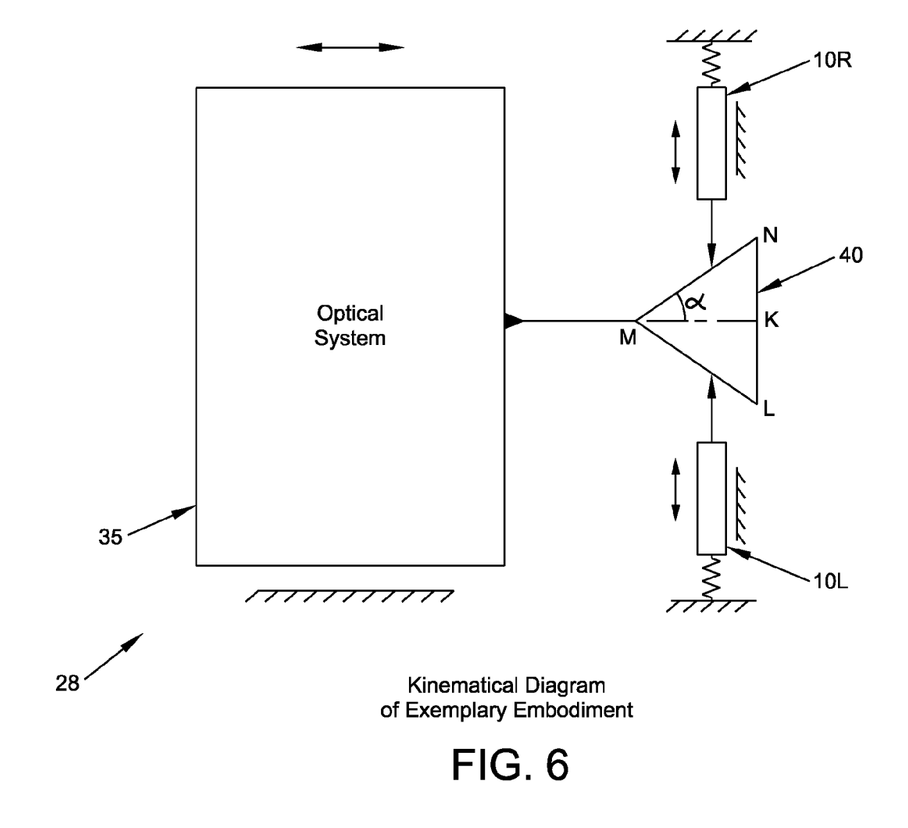
FIG. 6 is a schematic view of selected aspects of a novel stereoscopic visualization system formed in accordance with the present invention, wherein the stereoscopic visualization system is configured to adjust parallax by adjusting the physical dispositions of the left image sensor and the right image sensor in accordance with the focal point of the stereo endoscope system.

FIG. 6 shows a kinematical diagram of an exemplary embodiment of this form of the invention. In the exemplary embodiment of FIG. 6, there is shown selected aspects of the novel stereo camera 28. In this form of the invention, the optical system 35 of the novel stereoscopic endoscope system 30 (i.e., optical system 15 of FIG. 3) is restricted to axial movement within the required focusing range. The optical system is rigidly linked to a linear cam 40 that may be of a cone or triangular prism shape. The image sensors 10L, 10R of novel stereo camera 28 are restricted to horizontal movement perpendicular to the axis MK and are bound to ride on the hypotenuse of the triangle MNK (or MKL respectively), for example using springs and point-contact actuators. The angle α is defined by the equation:

$$\alpha=\arctan(h/f) \qquad (4)$$

where:

h is half of the inter-axial distance between the left and right channel optical systems (20L, 20R in FIG. 3); and f is the effective focal length of optical system 35.

The schematic diagram shown in FIG. 6 is just one example of the possible implementations of this form of the invention. It is suitable for both motorized and manual focusing. Other embodiments are also possible. For example, the optical system 35 and sensors 10L, 10R may be driven by separate programmable motors. In this case, no physical cams 40 may be necessary as the motors can be programmed to maintain the equation (3) during focusing.

Novel Stereoscopic Video Camera Wherein Parallax is Adjusted by Using the Overscan Mode and Electronically Adjusting the Display Areas of the Left Image Sensor and the Right Image Sensor In another form of the present invention, no physical movement of image sensors 10L, 10R is necessary in order to adjust parallax in the system. Rather, in this form of the invention, parallax is electronically adjusted by adjusting the display areas of the left and right image sensors.

Figure 7:
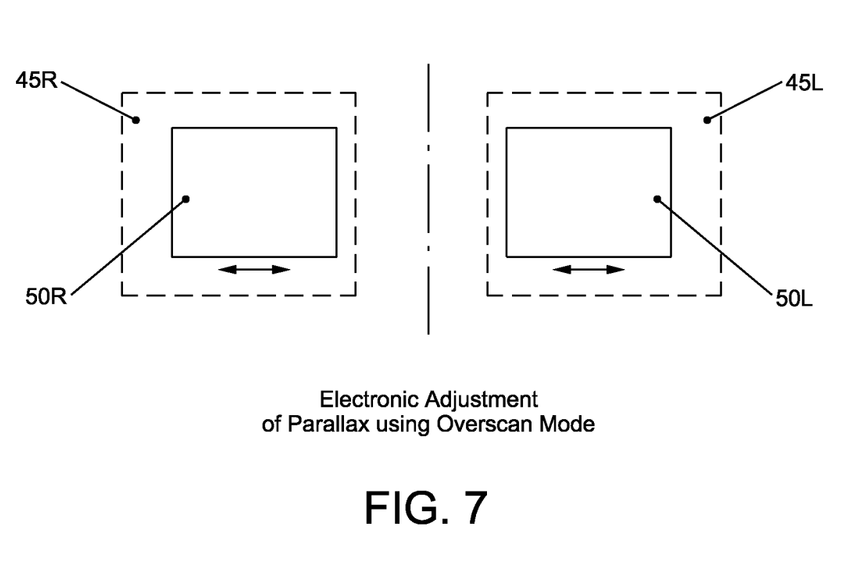
FIG. 7 is a schematic view of selected aspects of a novel stereoscopic visualization system formed in accordance with the present invention, wherein the stereoscopic visualization system is configured to adjust parallax by using the overscan mode and electronically adjusting the display areas of the left image sensor and the right image sensor.

More particularly, the principle of this embodiment is shown in FIG. 7. The image sensors 10L, 10R and the display device are configured so as to operate in the "overscan" mode, so that only part of the sensor imaging area 45L, 45R is actually displayed to the user. The system is programmed in such a way that the displayed areas 50L, 50R may change their positions as long as they remain within the image areas 45L, 45R of the image sensors 10L, 10R, respectively. In terms of horizontal parallax adjustment, the horizontal shift of the displayed areas 50L, 50R is equivalent to the physical offset of the sensors 10L, 10R in the construction shown in FIG. 6, i.e., the horizontal shift of the displayed areas 50L, 50R is to the extent appropriate to eliminate the parallax resulting from refocusing.

This form of the invention may be implemented in various embodiments. For instance, the stereo video camera may have a manual focusing mechanism for the optical system, and this manual focusing mechanism may be provided with position sensing means. The position sensing means electronically supply real-time information on the displacement Δs' of the optical system. The camera processing unit uses this information to shift the displayed areas 50L, 50R of left and right sensors 10L, 10R by distances Δh' in opposite directions according to equation (3). Alternatively, the camera focusing may be motorized and the information from the motor control circuitry may be fed into the camera processor. The system is programmed in such a way that displayed area shift and the focusing system displacement are linked by equation (3). The image sensors 10L, 10R may be mechanically offset for the initial position of the convergence point or the entire parallax adjustment may be done electronically.

An additional benefit of electronic adjustment of the parallax is the ease of changing the parameters of equation (3), i.e., in this form of the invention, such parameter changes may be effected by software means alone. This feature is especially useful in endoscopic applications where different optical systems (e.g., endoscopes) may be used with the same basic camera. The camera system may be supplied with means for recognizing the type of endoscope which is being used with the camera, or the type of endoscope family (having the same focal length f and inter-axial distance h) which is being used with the camera. These parameters may be automatically fed into the camera processor at initialization, and the parallax may then be automatically adjusted per equation (3) with a specific set of parameters for each family of endoscopes.

This form of the invention is particularly well suited to constructions utilizing a so-called "chip on the tip" stereo endoscope design, since it requires no moving mechanical parts.

Figure 8:
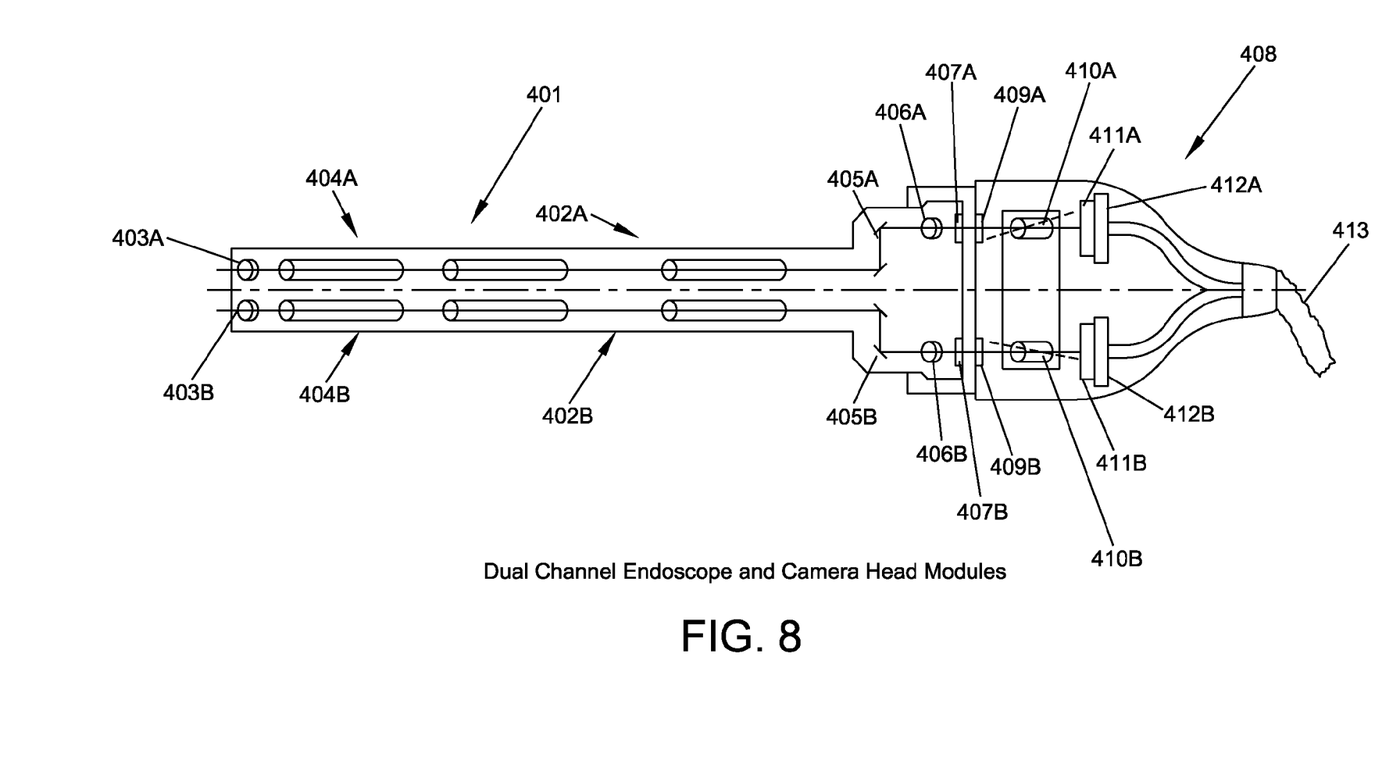
FIG. 8 is a schematic view of selected aspects of a novel stereoscopic visualization system formed in accordance with the present invention, wherein the stereoscopic visualization system is configured to adjust parallax by adjusting the physical dispositions of the optical components upstream of the left image sensor and the right image sensor.
Figure 9:
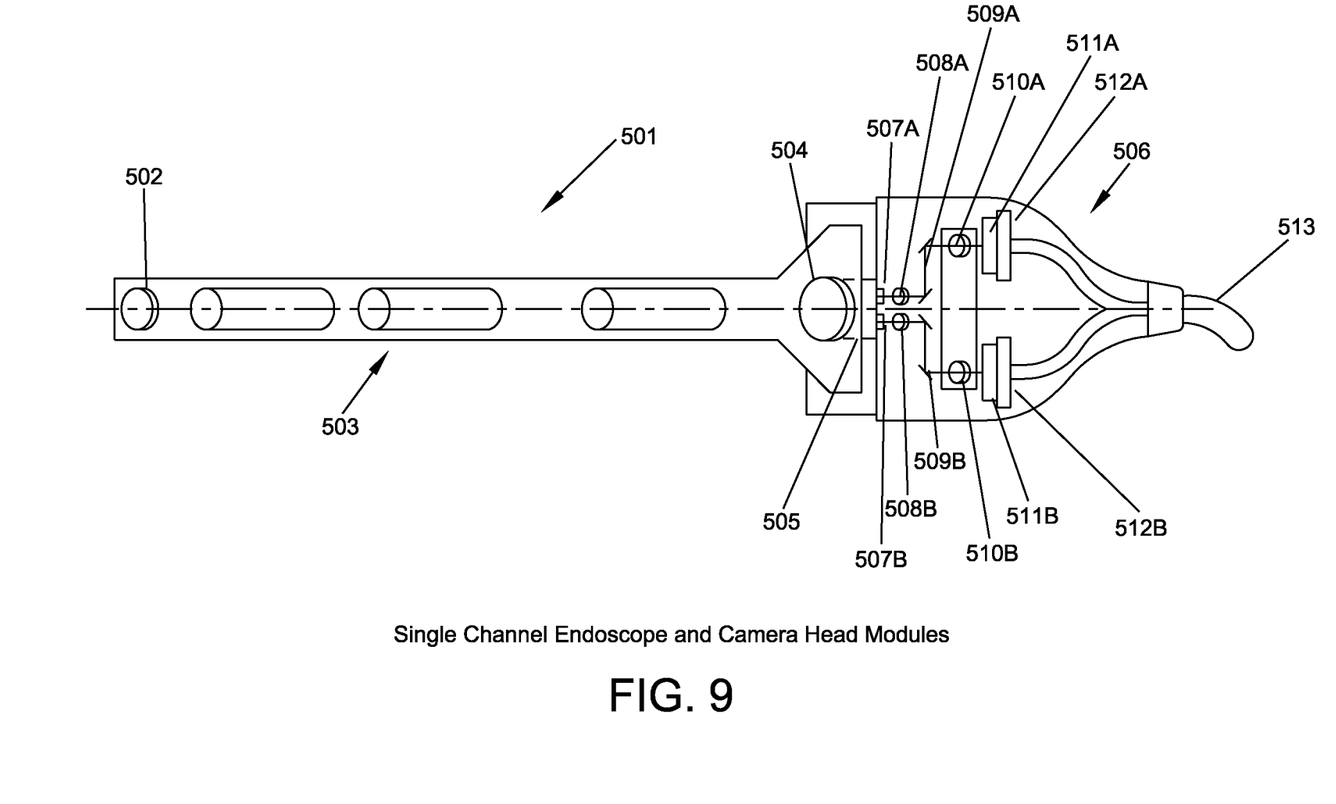
FIG. 9 is a schematic view of a novel single channel endoscope and camera head module, wherein the camera head module is configured so that parallax is adjusted by adjusting the physical dispositions of the optical components upstream of the left image sensor and the right image sensor.

Modular System Comprising an Endoscope and a Stereo Camera Detachably Coupled to Each Other For endoscopic applications, it is often advantageous to have a modular system comprised of an endoscope and a stereo camera detachably coupled to each other. The modularity of the system allows for coupling different types/sizes of endoscopes to the same stereo camera. Typically in endoscopic applications, the stereo camera is also divided into at least two modules: a hand-held camera head containing the image sensors with their driver circuitry, and a camera control unit containing the power supply, signal processing circuitry and video output connectors. The camera head is typically connected to the camera control unit via a cable or a wireless link. The camera control unit is itself connected to a display device. The presence of a separate camera control unit is typical but not absolutely necessary—the camera head may contain all of the camera circuitry and a portable (e.g., battery) power supply. FIGS. 8 and 9 schematically show two examples of coupled endoscope/camera head modules (the camera control unit is not shown in the figures).

In FIG. 8 the endoscope 401 is a dual-channel stereo endoscope. Endoscope 401 comprises two separate optical channels 402A, 402B extending from the distal end of the endoscope to the proximal end of the endoscope. At the distal end of the endoscope, each channel 402A, 402B contains an objective 403A, 403B forming the image of an object under observation. The images formed by the objectives 403A, 403B are relayed to the proximal end of endoscope 401 by optical relay systems 404A, 404B. Each relay system 404A, 404B may comprise one or a plurality of lens relays (typically rod-lens relays) or a coherent image fiber bundle. At the proximal end the endoscope, there may be provided channel separation systems 405A, 405B which may be formed by mirrors or prisms or combinations of both. Proximal to the channel separation systems, each channel contains an ocular lens 406A, 406B. Ocular lenses 406A, 406B form approximately collimated light beams exiting from exit ports 407A, 407B. Typically endoscope 401 represents a stand-alone, sealed, sterilizable device that detachably couples to the camera head 408.

The camera head module 408 depicted in FIG. 8 is preferably a sealed, sterilizable assembly. Camera head module 408 contains two optical ports 409A, 409B for receiving light beams from the left and right channels of endoscope 401. Focusing lenses 410A, 410B focus the light from the corresponding optical channels onto the image sensors 411A, 411B, respectively. To attain focusing, the lenses 410A, 410B move axially as a unit until the best focus for the desired object in front of endoscope 401 is achieved. Image sensors 411A, 411B are connected to their driver circuitries 412A, 412B so as to produce raw electrical signals representative of the optical image received by each image sensor 411A, 411B. The raw sensor signals are then sent to the camera control unit module (not shown) for signal processing via a cable 413 or a wireless link.

For the system shown in FIG. 8, there are several possibilities for maintaining a match between convergence in the central portion of the monitor and the best focus.

One possibility is the lateral movement of image sensors 411A, 411B away from and towards the symmetry line of FIG. 8 in correspondence with the axial movement of focusing group 410A, 410B, i.e., physically moving the image sensors to reduce parallax, in the manner described above in connection with FIG. 6. In this form of the invention, image sensors 411A, 411B move symmetrically according to equation (3) as a linear function of the axial movement of the focusing group. In this case the value f shall be interpreted as the effective focal length of the focusing lens 410A or 410B.

Yet another alternative implementation is based on electronic manipulation of the screen parallax as discussed above in connection with FIG. 7. In this form of the invention, the axial position of focusing lenses 410A, 410B may be monitored and registered by electronic means well known in the art (e.g., positioning sensors). Each position of the focusing lens group corresponds to a certain focal point and to a certain screen parallax at the point of best focus. As established in the above discussion, the function between the lens axial position and the value of parallax is linear. This function may be programmed or stored as a look-up table. Consequently, in order to maintain zero parallax matching for the focused area in the center of the screen, the electronic detection data of the position of the focusing group is supplied to the software means that control the electronic offset of the two channels.

Novel Stereoscopic Video Camera Wherein Parallax is Adjusted by Adjusting the Physical Dispositions of the Optical Components Upstream of the Left Image Sensor and the Right Image Sensor In the preceding sections, it is disclosed that parallax may be adjusted by physically moving the left and right image sensors so as to maintain the correlation between focus and vergence. However, in the respect it should be appreciated that, typically, image sensors 411A, 411B are permanently affixed to printed circuit boards containing driver electronics and other related circuitry. In many cases for high image quality applications, each image sensor represents a block of 3 individual sensors for Red, Green and Blue colors mounted on a color-separating prism. So, in practice, image sensors 411A, 411B may constitute complex electro-opto-mechanical assemblies that do not easily lend themselves to physical movement. Thus, this approach may not be practical for some situations.

An alternative, and sometimes more practical, approach is to introduce a lateral component to the travel of the focusing lens group 410A, 410B in order to adjust parallax. In this approach, the focusing lenses 410A, 410B travel in unison along the dashed lines inclined to the median axis of symmetry as shown in FIG. 8.

It should be noted that travel of the focusing lenses along the inclined segments may be the most practical way to adjust parallax without moving image sensors 411A, 411B, but it is not the only possible solution to achieve the objective of changing parallax during focusing. For example, lateral movements of ocular lenses 406A, 406B will result in parallax change; and lateral movement of channel separation components 405A, 405B will also cause a change of parallax; and unison lateral movement of combinations of elements 405A, 406A and elements 405B, 406B will cause a change of parallax; and swinging of the reflective surfaces of the channel separation components 405A, 405B in the plane of FIG. 8 will also result in a change in parallax. Thus it will be seen that, in another form of the present invention, parallax may be adjusted by adjusting the physical dispositions of the optical components upstream of the left and right image sensors.

Adjusting Parallax Independently of, and Decoupled from, Focusing

In essence, all of the techniques described above for adjusting parallax introduce a fixed amount of screen parallax to the entire scene. This is equivalent to moving the image towards the "behind the screen" direction or towards the "in front of the screen" direction. In some instances the exact match between the best focus area and convergence on the screen is not required, or it may be outweighed by other factors affecting perception of the stereo image. For example, part of the scene may contain objects having excessive parallax that cannot be visually fused by the user. Under such circumstances, it may be more important to maintain the "entire screen parallax budget" within the limits fusable by the user than to try to achieve exactly zero parallax for the focused objects in the center of the screen.

There may also be other reasons to decouple eye accommodation and vergence, e.g., a user preference to have most of the image behind the screen regardless best focus.

Therefore, other embodiments of the present invention include an adjustment of the screen parallax that is independent of, and decoupled from, focusing. This adjustment may be performed by all the methods already described above, such as the physical lateral displacement of the image sensors, or electronic shifts of the images on the display, or the physical lateral displacement of the optical components upstream of the image sensors, etc.

The adjustment of parallax may be viewer controlled, according to the viewer's preference, via user interface means of the sort known in the art, e.g., knobs, buttons, on-screen display sliders, etc.

It is also possible to compare left and right channel images (or specific regions of interest) by software means and derive parallax data, e.g. maximum values of positive and negative parallax. Then the adjustment of parallax, using the various approaches described above, may be made based on the parallax data and certain optimization criteria, for example, bringing the absolute value of parallax below a predetermined limit. In fact, bringing parallax to a zero value in the central portion of the image may be one of the criteria. The camera may also have an autofocus feature to ensure that the central portion of the image is always in focus. The user may have a choice of criteria for the parallax adjustment that could be implemented in the form of the user interface menu. In this embodiment, the adjustment of parallax may be done automatically via software without user intervention.

Thus, in one form of the invention, a "region of interest" may be defined on the screen (either by the viewer at the time of use, by the manufacturer at the time of manufacture, etc.). Then the system is configured to determine the range of parallax values within the region of interest (e.g., by comparing the relative position of at least some homologous points on the two image sensors). This information can then be used to adjust parallax according to some desired criteria. Such criteria might include, but is not limited to: (i) limiting parallax to some maximum negative value, (ii) limiting parallax to some maximum positive value, (iii) adjusting parallax to zero at some point on the screen (e.g., the middle of the screen), etc.

By way of example but not limitation, suppose it is determined that parallax in the region of interest ranges from −50 pixels to +150 pixels, and suppose it is determined that the maximum negative parallax should not exceed −30 pixels. In this case, the system might adjust parallax by a positive 20 pixels, e.g., by physically moving the image sensors laterally so as to reduce negative parallel parallax by 20 pixels, or electronically shifting the image so as to reduce negative parallel parallax by 20 pixels, or by physical moving the upstream optics so as to reduce negative parallax by 20 pixels, etc.

In the foregoing example, parallax is expressed in the context of sensor pixels. However, it will be appreciated that parallax can also be expressed in the context of length measurements on the display, or in angular measure, in which case it is necessary to identify the size of the display and the distance of the viewer from the display, etc. In this context, suppose parallax in the region of interest ranges from −30 mm to +70 mm, and it is determined that the maximum positive parallax should not exceed 64 mm, then the system might adjust parallax by reducing the maximum positive parallax by 6 mm.

Among other things, it will be appreciated that it may be desirable to adjust parallax so that the image displayed to the viewer remains visually fusable by the viewer, even if the normal link between focus and convergence should be strained. In this respect it will be appreciated that so long as the relationship between focal distance and vergence distance remains within certain bounds (FIG. 2), the viewer will remain in their visual "zone of comfort" (i.e., the so-called Percival's zone of comfort).

In one preferred form of the invention, the novel stereoscopic visualization system can be configured so that it normally adjusts parallax to zero for the center of the screen (i.e., typically the region of proper focus), unless some portion of the image cannot be visually fused by the user. In this case, the stereoscopic visualization system can be configured to adjust the parallax values of the image so that they remain within the ranges needed to make the entire image visually fusable by the user, even if parallax is not adjusted to zero for the center of the screen.

It should be noted that comparison of the left and right images, and deriving the parallax data, constitutes a computer intensive process. Performing this operation continuously at the video frame rate may not be practical in some situations. However, since in endoscopic applications the scene changes are relatively slow, it can be sufficient to perform the comparison computation at relatively infrequent intervals compared to the video rate (e.g., once in 1 second). To prevent excessive amounts of parallax adjustment that may result in too frequent and jittery movement of the image in and out of the screen, the optimized thresholds can be imposed in the software to enable adjustment only after substantial changes in the parallax data occur within the region of interest.

Furthermore, it should also be appreciated that determinations of parallax within the region of interest should exclude the visual aspects of transient events which are not core to the image being assessed. By way of example but not limitation, in a typical endoscopic application, the surgical procedure might involve electrocautery, which is commonly accompanied by transient visual occurrences such as liquid bubbling, vapor discharges, etc. In such a situation, these transient visual occurrences should be excluded from the parallax determination in order to ensure proper calculation of parallax. In this respect it will be appreciated that a proper determination of parallax should be directed to relatively stable regions of the image.

Modular Construction Comprising a Single-Channel Stereo Camera

FIG. 9 shows an alternative version of the endoscope/camera head modules where endoscope 501 is of a single-channel type. Preferably the single-channel endoscope is specifically designed for stereoscopic endoscopy for increased stereo perception, although a regular endoscope may also be used. Optically, from distal end to proximal end, the single-channel endoscope includes an objective lens 502 forming the image of an object under observation; and the image formed by objective lens 502 is relayed to the proximal end of endoscope 501 by a relay system 503. The relay system may comprise one or a plurality of lens relays (typically rod-lens relays) or a coherent image fiber bundle. At the proximal end of the endoscope, there is an ocular lens 504. Ocular lens 504 forms an approximately collimated light beam 505 exiting the endoscope module 501. Typically the endoscope module 501 represents a stand-alone, sealed, sterilizable device that detachably couples to the camera head module 506.

The camera head module 506 contains two optical ports 507A, 507B that are located within the cross-section of the light beam 505. Optical ports 507A, 507B "cut out" narrow pencils of light from the beam 505. These narrow pencils of light, if traced back through the optical train of the endoscope, will result in two pencils of light entering the endoscope at two different angles from the object under observation. That is how stereoscopic imaging is obtained with the single channel endoscope. The camera head 506 also include a channel separation system containing lenses 508A, 508B and mirror systems (or prisms) 509A, 509B. The light from the left and right channels are focused by focusing lenses 510A, 510B onto image sensors 511A, 511B. The image sensors are coupled to driver circuitry boards 512A, 512B that generate electrical signals representative of optical images received by the image sensors. These electrical signals are sent to the camera control unit (not shown) for further processing via a cable 513 or a wireless link.

All of the aspects of the invention discussed above with regard to the dual-channel scope/camera head configuration depicted in FIG. 8 are equally applicable to the single channel scope/camera configuration shown in FIG. 9.

ADDITIONAL NOTES

It should be appreciated that the schematic nature of the foregoing description should not be construed to limit the general nature of the invention. All of the optical elements schematically shown as a single lens or mirror surface may in actual implementation represent a compound lens group or prism block without limitations. The image sensors schematically shown as a single sensor may represent a 3-chip sensor block with color-separating prism. The modular structure of the system may also vary. For instance, the focusing optics may be included in a separate sealed, sterilizable module (often called an "endo-coupler") that detachably couples to the camera head at the proximal end and detachably couples to the endoscope at the distal end. The color separation and ocular components shown in FIG. 8 as part of the endoscope module may be made a part of the camera head module or the endo-coupler module. Or the entire assemblies shown in FIGS. 8 and 9 may be made as single sealed modules with no user-detachable parts. Furthermore, the display may be a 3D monitor of the sort well known in the art, or a head-mounted display or any other display device capable of presenting the left and right images to the appropriate eye of the viewer. In display devices comprising associated optical systems such as a head-mounted display, the distance to the display is considered to be the distance from the eye of the viewer to the image produced by the optical system of the display.

MODIFICATIONS

While the present invention has been described in terms of certain exemplary preferred embodiments, it will be readily understood and appreciated by one of ordinary skill in the art that it is not so limited, and that many additions, deletions and modifications may be made to the preferred embodiments discussed above while remaining within the spirit and scope of the present invention.

What is claimed is:
1. Apparatus for presenting a stereoscopic image to a viewer, the apparatus comprising:
    an endoscope; and
    a stereoscopic video camera optically connected to the endoscope, wherein the stereoscopic video camera comprises:
        first and second optical channels for acquiring, respectively, first and second images of a scene from the endoscope, the first and second optical channels comprising first and second focal points, respectively;
        first and second image sensors for acquiring, respectively, the first and second images from the first and second optical channels, the first and second image sensors being positioned along an axis; and parallax adjusting means for adjusting the parallax of a stereoscopic image acquired by the first and second image sensors and presented on a display;

wherein the first and second optical channels each comprise at least one optical component, and further wherein the parallax adjusting means comprises optical component movement means for simultaneously moving, longitudinally and laterally, the at least one optical component of each of the first and second optical channels so as to laterally shift the output of the first and second optical channels relative to the axis of the first and second image sensors in accordance with changes in the first and second focal points, whereby to simultaneously adjust focus and parallax.

2. Apparatus according to claim 1 wherein the parallax adjusting means comprises sensor movement means for physically moving at least one of the first and second image sensors along the axis.

3. Apparatus according to claim 2 wherein the apparatus comprises focusing means for adjusting the dispositions of the first and second focal points, and further wherein the sensor movement means is configured to operate in conjunction with the focusing means.

4. Apparatus according to claim 2 wherein the apparatus comprises focusing means for adjusting the dispositions of the first and second focal points, and further wherein the sensor movement means is configured to operate independently of the focusing means.

5. Apparatus according to claim 2 wherein the sensor movement means comprises at least one cam and at least one cam follower.

6. Apparatus according to claim 2 wherein the sensor movement means comprises at least one motor.

7. Apparatus according to claim 2 wherein the sensor movement means is configured to physically move both of the first and second image sensors along the axis.

8. Apparatus according to claim 1 wherein each of the first and second image sensors defines a plane, and further wherein the planes of the first and second image sensors are aligned along the axis.

9. Apparatus according to claim 1 wherein each of the first and second image sensors defines a plane, and further wherein at least one of the planes of the first and second image sensors is disposed at an acute angle to the axis.

10. Apparatus according to claim 1 wherein the apparatus comprises focusing means for adjusting the dispositions of the first and second focal points, and further wherein the optical component movement means is configured to operate in conjunction with the focusing means.

11. Apparatus according to claim 1 wherein the apparatus comprises focusing means for adjusting the dispositions of the first and second focal points, and further wherein the optical component movement means is configured to operate independently of the focusing means.

12. Apparatus according to claim 1 wherein the optical component movement means comprises at least one cam and at least one cam follower.

13. Apparatus according to claim 1 wherein the optical component movement means comprises at least one motor.

14. Apparatus according to claim 1 wherein the apparatus further comprises mapping means for mapping the first and second images acquired by the first and second image sensors to a display according to a pre-determined positional relationship, and further wherein the parallax adjusting means is configured to modify the manner in which the mapping means maps the first and second images to the display.

15. Apparatus according to claim 14 wherein the parallax adjusting means is configured to cause a lateral shift in at least one of the first and second images when the mapping means maps the first and second images to the display.

16. Apparatus according to claim 14 wherein the parallax adjusting means is configured to cause the mapping means to present only a portion of the first and second images acquired by the first and second image sensors to the display.

17. Apparatus according to claim 16 wherein the first and second optical channels comprise first and second focal points, respectively, wherein the apparatus comprises focusing means for adjusting the dispositions of the first and second focal points, and further wherein the parallax adjusting means is configured to operate in conjunction with the focusing means.

18. Apparatus according to claim 16 wherein the first and second optical channels comprise first and second focal points, respectively, wherein the apparatus comprises focusing means for adjusting the dispositions of the first and second focal points, and further wherein the parallax adjusting means is configured to operate independently of the focusing means.

19. Apparatus according to claim 14 wherein the parallax adjusting means is configured to determine parallax values existing within a region of interest in the first and second images, and then adjust parallax in accordance with a selected criteria.

20. Apparatus according to claim 19 wherein the parallax adjusting means is configured to limit parallax within the region of interest to a maximum negative value.

21. Apparatus according to claim 19 wherein the parallax adjusting means is configured to limit parallax within the region of interest to a maximum positive value.

22. Apparatus according to claim 19 wherein the parallax adjusting means is configured to adjust parallax to zero for a selected portion of the display.

23. Apparatus according to claim 22 wherein the selected portion of the display is the central portion of the display.

24. Apparatus according to claim 19 wherein the parallax adjusting means is configured to adjust parallax such that the relationship between the focal distance of the apparatus and the vergence distance of the display remains within a selected range.

25. Apparatus according claim 19 wherein the selected criteria takes into account at least one of the distance of the viewer from the display, and the size of the display, and the stereo base of the optical system.

26. Apparatus according to claim 19 wherein the parallax adjusting means is configured to adjust parallax to zero for a selected portion of the display if the relationship between the focal distance of the apparatus and the vergence distance of the display remains within a selected range, otherwise the parallax adjusting means is configured to adjust parallax such that the relationship between the focal distance of the apparatus and the vergence distance of the display remains within a selected range.

27. Apparatus according to claim 19 wherein the selected criteria is established in advance of viewing.

28. Apparatus according to claim 19 wherein the selected criteria is established by the viewer at the time of viewing.

29. Apparatus for presenting a stereoscopic image to a viewer, the apparatus comprising:

a stereoscopic video camera comprising:
> first and second optical channels for acquiring, respectively, first and second images of a scene, the first and second optical channels comprising first and second focal points, respectively;
> first and second image sensors for acquiring, respectively, the first and second images from the first and second optical channels, the first and second image sensors being positioned along an axis; and
> parallax adjusting means for adjusting the parallax of a stereoscopic image acquired by the first and second image sensors and presented on a display;
> wherein the first and second optical channels each comprise at least one optical component, and further wherein the parallax adjusting means comprises optical component movement means for simultaneously moving, longitudinally and laterally, the at least one optical component of each of the first and second optical channels so as to laterally shift the output of the first and second optical channels relative to the axis of the first and second image sensors in accordance with changes in the first and second focal points, whereby to simultaneously adjust focus and parallax.

30. Apparatus according to claim 29 further comprising an endoscope, the endoscope being optically connected to the stereoscopic video camera.

31. A method for presenting a stereoscopic image to a viewer, the method comprising:

providing a stereoscopic video camera comprising:
> first and second optical channels for acquiring, respectively, first and second images of a scene, the first and second optical channels comprising first and second focal points, respectively;
> first and second image sensors for acquiring, respectively, the first and second images from the first and second optical channels, the first and second image sensors being positioned along an axis; and
> parallax adjusting means for adjusting the parallax of a stereoscopic image acquired by the first and second image sensors and presented on a display;
> wherein the first and second optical channels each comprise at least one optical component, and further wherein the parallax adjusting means comprises optical component movement means for simultaneously moving, longitudinally and laterally, the at least one optical component of each of the first and second optical channels so as to laterally shift the output of the first and second optical channels relative to the axis of the first and second image sensors in accordance with changes in the first and second focal points, whereby to simultaneously adjust focus and parallax; and operating the stereoscopic video camera so as to provide a stereoscopic image to the user wherein focus and parallax have been adjusted.

* * * * *